(12) United States Patent
Vischer et al.

(10) Patent No.: US 9,138,516 B2
(45) Date of Patent: Sep. 22, 2015

(54) APPARATUS AND METHOD FOR RECOGNIZING COUPLINGS BETWEEN TWO SYSTEM COMPONENTS

(71) Applicant: MEDELA HOLDING AG, Baar (CH)

(72) Inventors: Peter Vischer, Küssnacht am Rigi (CH); Urs Koch, Greppen (CH); Daniela Wäckerlin, Baar (CH)

(73) Assignee: MEDELA HOLDING AG, Baar (CH)

( * ) Notice: Subject to any disclaimer, the term of this patent is extended or adjusted under 35 U.S.C. 154(b) by 190 days.

(21) Appl. No.: 13/737,647

(22) Filed: Jan. 9, 2013

(65) Prior Publication Data

US 2013/0123687 A1    May 16, 2013

Related U.S. Application Data

(62) Division of application No. 13/023,980, filed on Feb. 9, 2011, now abandoned.

(30) Foreign Application Priority Data

Feb. 11, 2010   (CH) ...................................... 0166/10

(51) Int. Cl.
*A61M 1/06* (2006.01)
*A61M 1/00* (2006.01)
*A61M 39/10* (2006.01)

(52) U.S. Cl.
CPC ............... *A61M 1/06* (2013.01); *A61M 1/0023* (2013.01); *A61M 1/0066* (2013.01); *A61M 39/10* (2013.01); *A61M 2039/1027* (2013.01); *A61M 2039/1044* (2013.01); *A61M 2205/27* (2013.01); *A61M 2205/60* (2013.01); *A61M 2205/6054* (2013.01)

(58) Field of Classification Search
CPC ............ A61M 2039/1027; A61M 2039/1044; A61M 2205/27; A61M 2205/60; A61M 2205/6054; A61M 1/0025; A61M 1/06; A61M 1/062
USPC ............... 604/74, 76, 523, 533; 235/375, 382
See application file for complete search history.

(56) References Cited

U.S. PATENT DOCUMENTS

| | | | | |
|---|---|---|---|---|
| 5,460,490 A | * | 10/1995 | Carr et al. | 417/44.2 |
| 6,626,355 B2 | * | 9/2003 | Sasse et al. | 235/375 |
| 7,237,990 B2 | * | 7/2007 | Deng | 409/175 |
| 2006/0073048 A1 | * | 4/2006 | Malackowski | 417/474 |
| 2009/0099552 A1 | * | 4/2009 | Levy et al. | 604/533 |
| 2011/0315757 A1 | * | 12/2011 | Colman et al. | 235/375 |

* cited by examiner

*Primary Examiner* — Quynh-Nhu H Vu
(74) *Attorney, Agent, or Firm* — McDonnell Boehnen Hulbert & Berghoff LLP

(57) ABSTRACT

In an apparatus for recognizing couplings between a first and a second component of a system, one of the two components is provided with an identification unit. A checking unit is operatively connected to the second component. The identification unit contains an item of information relating to the first component. The checking unit is designed for recognizing and processing this item of information. The checking unit moreover is designed such that, as a function of a result of the processing of the item of information, it allows or prevents coupling between the first and the second component. This apparatus enables a combined use of system components only in the case of an admissible coupling thereof.

18 Claims, 4 Drawing Sheets

APPARATUS AND METHOD FOR RECOGNIZING COUPLINGS BETWEEN TWO SYSTEM COMPONENTS

CROSS REFERENCE TO RELATED APPLICATIONS

The present application is a divisional of U.S. patent application Ser. No. 13/023,980, filed Feb. 9, 2011, which claims priority to Swiss Patent Application No. 00166/10, filed Feb. 11, 2010. The entire disclosure contents of these applications are herewith incorporated by reference into the present application.

TECHNICAL FIELD

The present invention relates to an apparatus and a method for recognizing couplings between two components of a system.

BACKGROUND

Conventionally, coupling between two system components is always enabled when two coupling parts, which should establish the connection between the two system components, complement one another physically and form two parts of a unit. This can easily be seen on the basis of a plug-in connection.

However, this criterion is often insufficient, particularly in the field of medical technology. Thus, for example, US 2006/0073048 discloses an irrigation pump with a replaceable tubing set and a control console. The tubing set comprises a radio-frequency identification (RFID) apparatus in which physical attributes of the tubing set are stored. A control console reads this data and, taking into account further data, makes a decision as to whether the pump together with this tubing set is suitable for discharging the desired amount of liquid. Moreover, the control console can also check whether the pump manufacturer has even approved the tubing set for use with the manufacturer's pump by using manufacturer identification.

U.S. Pat. No. 5,460,490 likewise describes an irrigation and suction pump with a plurality of tubing sets. The various tubing sets are each only designed for a specific use and encoded appropriately. The pump has corresponding recognition means for reading these codes.

U.S. Pat. No. 7,237,990 shows a surgical cutting instrument with RFID in the handle for interchanging data between blade and handle.

WO 03/013372 discloses a surgical system with a handle and with accessories that can be attached to the handle. In this case, a chip is also arranged in the accessory for recognizing the accessory.

These known systems successfully avoid incorrect operational settings of the instruments because the system itself selects or at least proposes the mode of operation resulting from the combination of instrument and accessory.

However, should an attempt be made at connecting an incompatible accessory to the instrument, this can lead to physical damage to the instrument, particularly in the region of the coupling element thereof. Furthermore, it is not always ensured that the instrument cannot be used nonetheless.

SUMMARY

It is therefore an object of the invention to create an apparatus and a method for recognizing couplings between two components of a system, which permit a combined use of the system components only in the case of an admissible coupling thereof.

In the apparatus according to the invention for recognizing couplings between a first and a second component of a system, one of the two components is provided with an identification unit. A checking unit is operatively connected to the second component. The identification unit contains an item of information relating to the first component. The checking unit is designed for recognizing and processing this item of information. The checking unit moreover is designed such that, as a function of a result of the processing of the item of information, it allows or prevents coupling between the first and the second component.

In the method according to the invention for recognizing couplings between a first and a second component of a system, one of the two components contains an item of information relating to this first component, wherein a checking unit recognizes and processes this item of information and exerts an effect on the second component. As a function of a result of the processing of the item of information, the checking unit allows or prevents coupling between the first and the second component.

This ensures that it is only possible to create desired connections between the two system components, in particular a suction pump and an accessory, and that the system components can only be used together at all in the case of an admissible combination. This enables recognition of non-proprietary, unsuitable, outdated or otherwise unsuitable system components and their use or coupling can be avoided.

In addition, or alternatively, the checking unit can, as a function of a result of the processing of the item of the information, allow or prevent operation of the second component, which in this case is a suction pump.

Further embodiments are specified in the dependent claims.

BRIEF DESCRIPTION OF THE FIGURES

Preferred embodiments of the invention will be described in the following text on the basis of the drawings, which merely serve for explanatory purposes and should not be construed as limiting the invention. In the drawings.

DETAILED DESCRIPTION

Figure 1:
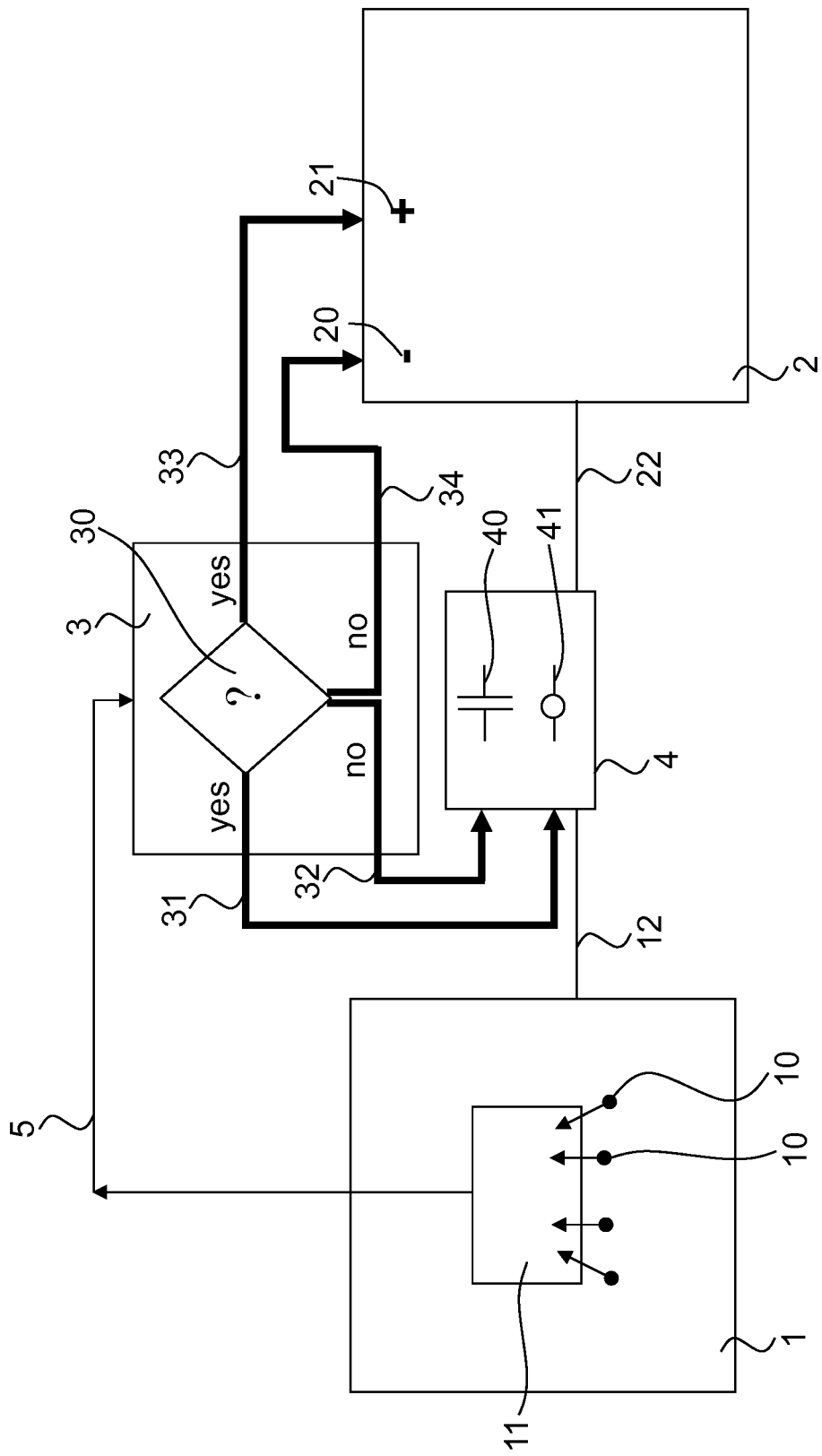
FIG. 1 shows a basic scheme of the apparatus according to the invention.

FIG. 1 illustrates a basic scheme of the apparatus according to the invention and also explains the method according to the invention.

A first system component 1 comprises an identification unit 11 storing at least one item of information, preferably a plurality of items of information, relating to properties 10 of this first system component 1.

A second system component 2 can be connected to the first system component 1 via a coupling unit 4. The coupling is preferably brought about by interconnecting a first and a second coupling part 12, 22.

A checking unit 3, also referred to as a controller, is equipped with a central intelligence or logic 30 and is operatively connected to the first and the second system component 1, 2.

If coupling should now be brought about between the first and the second system component 1, 2, the information or data stored in the identification unit 11 is transmitted to the checking unit 3. This is indicated in FIG. 1 by the reference sign 5. The transmission can be active and be brought about independently by the first system component 1, or it can be activated by the checking unit 3.

Information relating to the second system component 2 is stored in the checking unit 3. Alternatively, this information can likewise be queried or transmitted to the checking unit 3. The checking unit 3, in particular the logic 30, now checks whether the first system component 1 is suitable for connection to the second system component 2. A control variable is preferably determined by means of a suitable algorithm.

If the answer is "yes", coupling, i.e. a connection between the first and second coupling parts 12, 22, can now be permitted. The corresponding signal from the checking unit 3 to the coupling unit 4 is provided with the reference sign 31 in FIG. 1. The established coupling is labeled by the reference sign 41.

If the answer is "no", coupling is prevented. That is to say, the first and the second coupling part 1, 2 cannot be interconnected. The corresponding signal from the checking unit 3 to the coupling unit 4 is provided with the reference sign 32 in FIG. 1. The prevented coupling is labeled by the reference sign 40. By way of example, coupling can be prevented by not releasing a plug input, in particular by not allowing the removal of a protective plate from in front of a coupling element.

FIG. 1 additionally illustrates a further action of the checking unit 3. If the aforementioned answer is "yes", a signal is transmitted to the second system component 2 (see reference sign 33) and operation of the second system component 2 is permitted (see reference sign 21). If the aforementioned answer is "no", a signal is likewise transmitted to the second system component 2 (see reference sign 34) and operation of the second system component 2 is prevented (see reference sign 20).

It is also possible that, in the case of a "no" answer, no signal is transmitted and the coupling or the operation of the second system component 2 is simply not permitted.

The checking unit 3 is preferably integrated into the second system component 2 or at least arranged in a common housing. However, it can also be designed as a separate component with its own housing.

In a preferred embodiment of the apparatus according to the invention and in a preferred variant of the method according to the invention, both actions are brought about: i.e. both coupling and operation of the second system component 2 are allowed or prevented. In other embodiments, the apparatus is designed such that only one of the two actions is provided. That is to say, in a first embodiment, the apparatus can enable or prevent coupling. In a second embodiment, the apparatus can enable or prevent the operation of the second system component.

In the case where only the operation can be enabled or prevented, the second system component has a suction pump, wherein the operation of the latter is enabled or prevented. In this case, the first system component 1 is preferably suction tubing, for example drainage tubing or vacuum tubing.

In all examples, the second system component 2 is preferably a suction pump, e.g. a drainage pump for draining bodily fluids or a breastpump for expressing human breastmilk. By way of example, such drainage pumps are used in wound drainage, thorax drainage, operations and liposuctions.

In all examples, the first system component 1 is preferably an accessory for this suction pump. For example, it is a breast shield for a breastpump, vacuum tubing for the connection between the breast shield and breastpump, a vacuum-actuated wound insert, drainage tubing, secretion tubing, service tubing, a catheter or a fluid collection container.

In all embodiments, the first coupling element 12 and the second coupling element 22 are two complementary parts of a connection, e.g. a plug-in connection, a snap-on connection, a swivel connection, a bayonet connection, a magnetic connection or an electro-mechanical connection.

In all embodiments, the identification unit 11 is preferably part of the first system component or arranged together therewith in the same housing. By way of example, it can be arranged in the breast shield, in the fluid collection container, in or on the tubing, in or on the inner or outer wall of the tubing, on the interface between drainage container and drainage bag, or on the interface between drainage tubing and wound.

The recognition or identification is preferably not brought about mechanically but electronically. Radio-frequency identification (RFID) is preferably used, wherein the appropriate apparatus is provided in the checking unit 3. The transmission, recognition and/or processing of the information however can also be brought about electronically, optically or chemically. However, the information is preferably transmitted contactlessly.

The information and data stored in the identification unit 11 preferably relate to information from the manufacturer, such as make, classification, age of the system component or production date.

Figure 2:
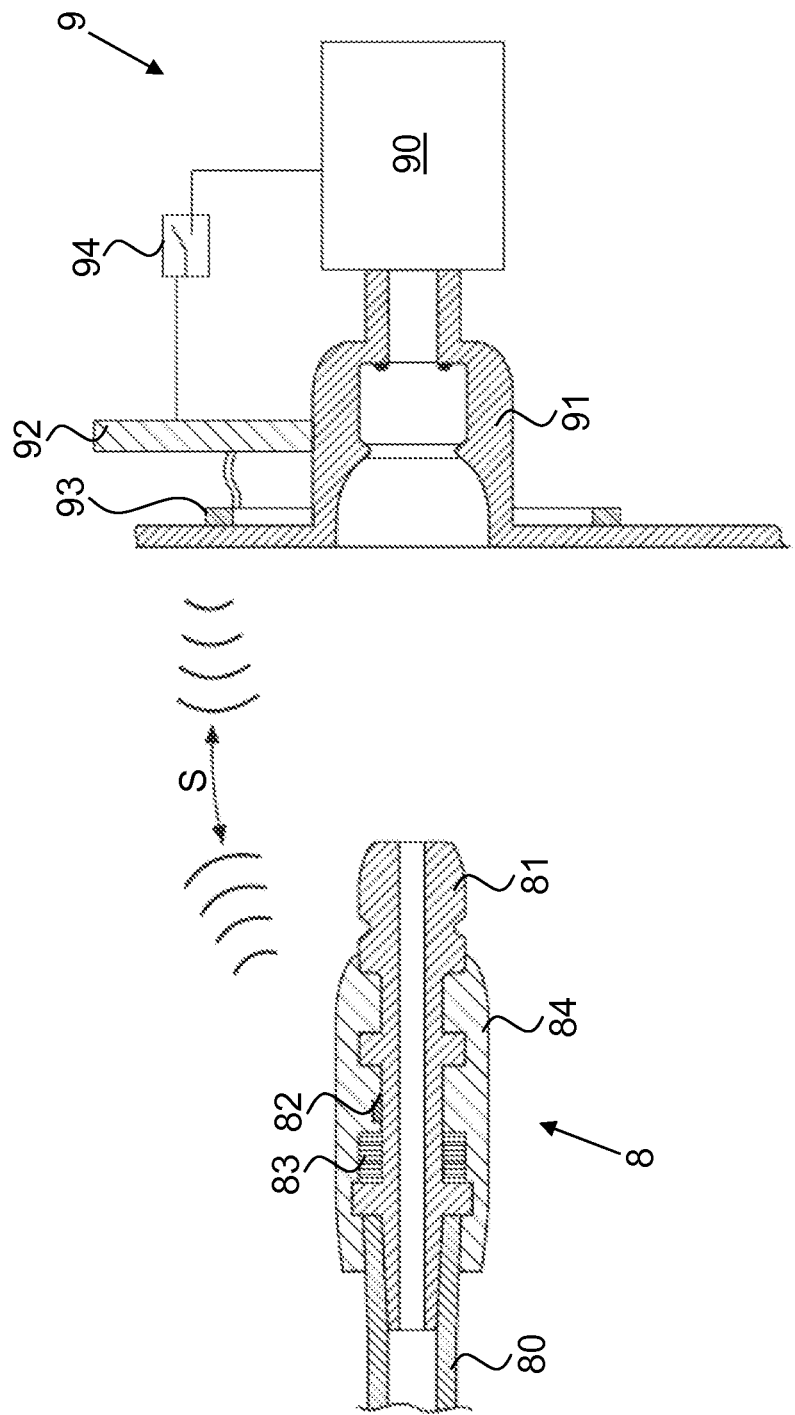
FIG. 2 shows a schematic illustration of the apparatus according to the invention in a first embodiment.

FIG. 2 illustrates a first application of the apparatus according to the invention. The first system component 8 is tubing 80 with a first plug part 81. An identification unit, in this case a microchip 82 with stored information and a transponder coil 83 for RFID, is arranged in a housing 84 of the plug 81.

In this case, the second system component 9 is a suction pump 90, the housing of which is provided with a second plug part 91 for connection to the first plug part 81. The first plug part 81 is preferably male; the second plug part 91 is preferably designed to be female.

Electronics 92 are provided with RFID or another contactless information query unit. An antenna 93 transmits the information transmitted by the first system component 8 to the checking unit, i.e. the electronics 92. Depending on the type of obtained information, the electronics now close a switch 94 or the latter remains open. If the switch 94 is open, operation of the suction pump is prevented. If it is closed, the suction pump can be operated and the tubing 80 can be actuated with negative pressure. Thus, in this example, operation of the second system component 2 is allowed or prevented, depending on whether the answer is "yes" or "no".

Figure 3:
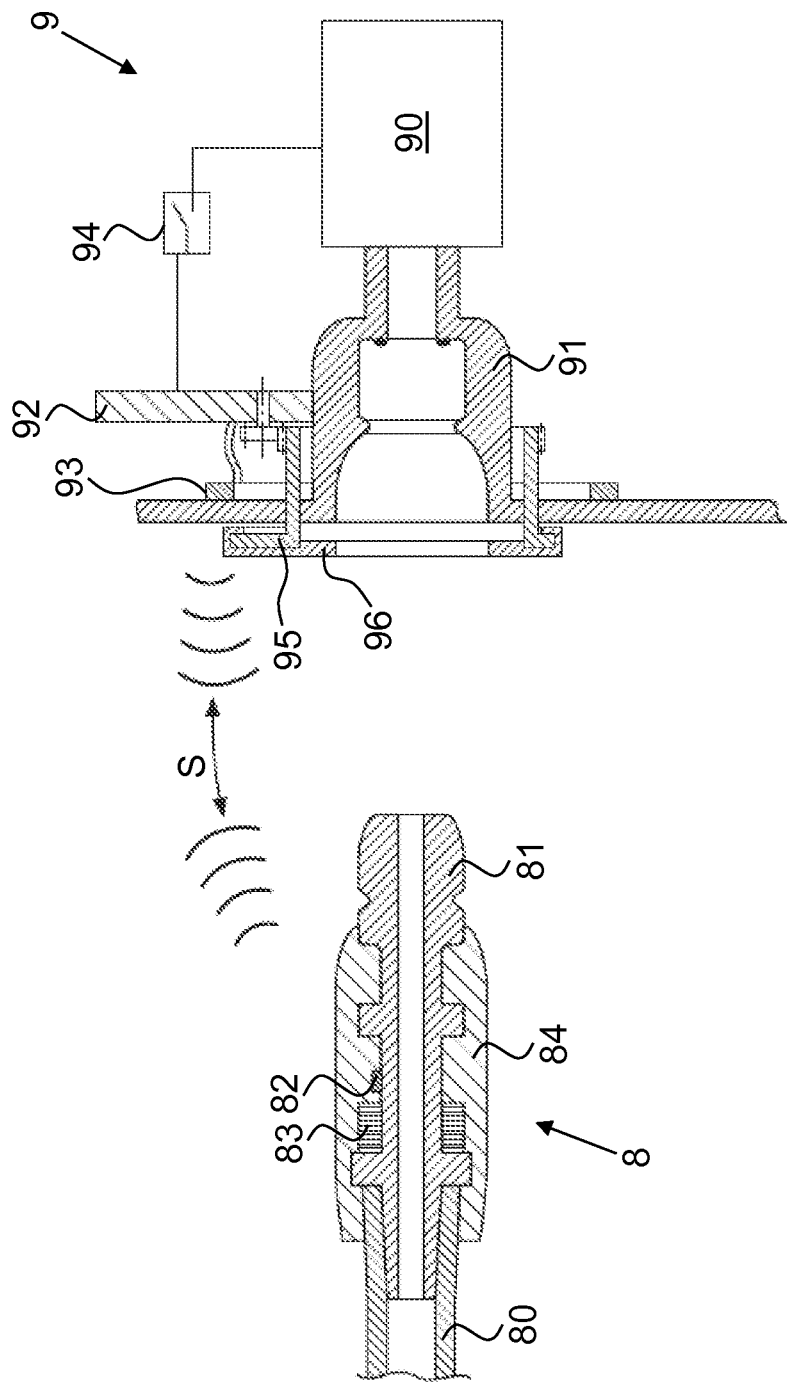
FIG. 3 shows a schematic illustration of the apparatus according to the invention in a second embodiment.

FIG. 3 illustrates a further embodiment which substantially has the same components as the embodiment as per FIG. 2. Therefore, identical parts have been provided with the same reference signs and will not be explained in any more detail here. However, in this case there is an additional apparatus that closes off the input of the female plug part 91. In this example, this apparatus comprises an eccentric wheel 95 and a sealing plate 96 operatively connected thereto. Other solutions are possible.

The input of the female plug part 91 is preferably sealed by the sealing plate 96 as standard and so the male plug part 81 cannot be inserted. The sealing plate 96 therefore acts as a barrier. If the answer to the query now is "yes", the electronics 92 cause the eccentric wheel 95 to move the sealing plate 96 by means of a drive (not illustrated here), and the input of the female plug part is released. Other variants are also possible. As a result of this, there can be coupling between the first and second system components. Since the answer "yes" has additionally closed the switch 94, the suction pump can also be operated.

Alternatively, there can be no switch 94 in the exemplary embodiment as per FIG. 3 and merely the input to the female plug part 91 can be locked.

Figure 4:
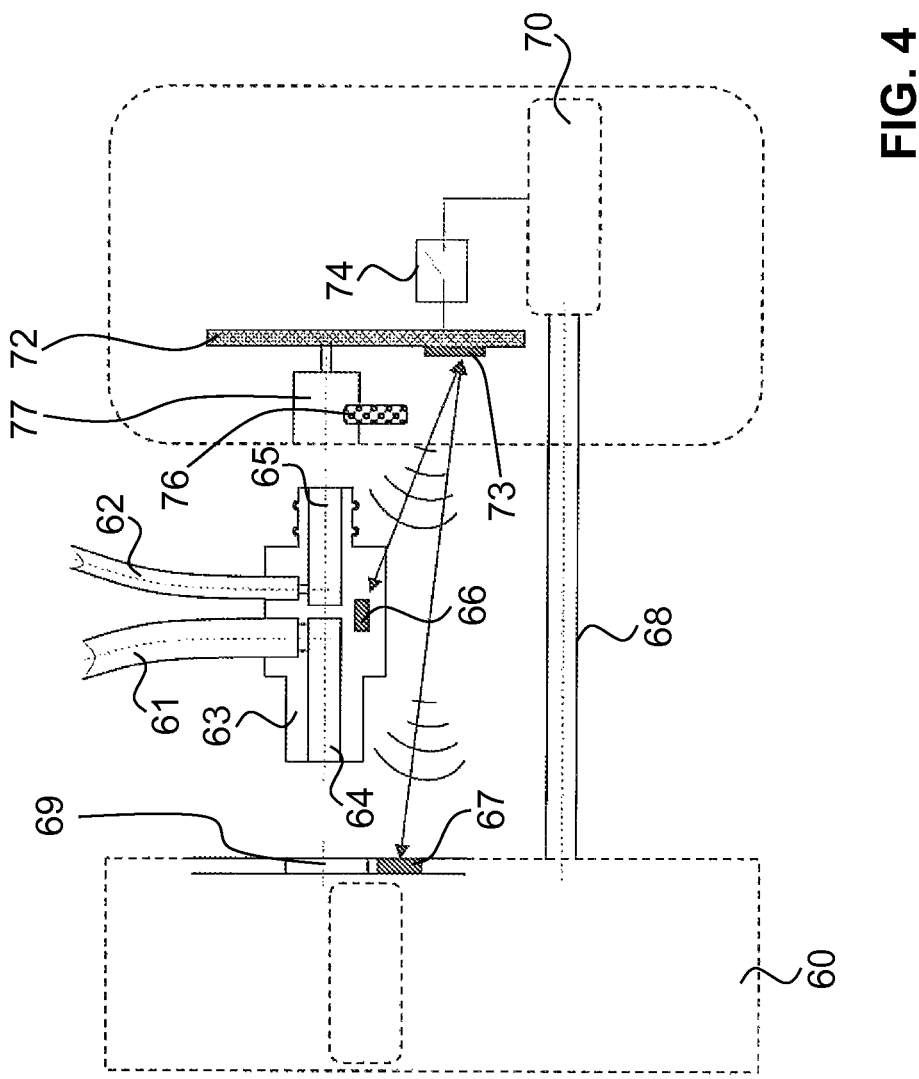
FIG. 4 shows a schematic illustration of the apparatus according to the invention in a third embodiment.

FIG. 4 illustrates a further exemplary embodiment, this time from the field of drainage apparatuses. The first system component is a drainage container 60 provided with a microchip 67. This microchip 67 stores data and information relating to the drainage container. The drainage container 60 is provided with a patient-side connection 69.

The second system component is a suction pump 70 connected to the drainage container 60 via a vacuum line or vacuum tubing 68. A checking unit or electronics 72 is/are arranged in the housing of the suction pump 70. Here too, a switch 74 is available in turn, which is connected to the electronics 72 and has to be closed in order to operate the suction pump. The electronics 72 are provided with RFID 73. The housing is provided with a patient-side connection 77, which can preferably be closed by means of a mechanical switch 76. The switch 76 is likewise actuated by means of the electronics 72.

The coupling unit is formed by a double plug 63, which connects the drainage container 60 to the suction pump 70. The 63 plug has a container-side connection 64, which can be plugged into the patient-side connection 69 of the drainage container 60, and a pump-side connection 65, which can be plugged into the patient-side connection 77 of the suction pump 70. Moreover, drainage tubing 61 and preferably service tubing 62 are plugged into the double plug 63. Arranged in the housing of the double plug 63, there is a microchip 66 that stores information and data relating to the double plug and, preferably, the tubing 61, 62. Thus, the double plug 63 forms not only a coupling unit but also, simultaneously, a further second system component.

The data from the two microchips 66, 67 of the two second system components 60, 63 are sent to the electronics 72 of the first system component 70 and are processed there, and the switch 74 is or is not opened, depending on the information obtained. Likewise, the mechanical switch 76, i.e. the barrier, is or is not opened, depending on the information obtained. In this example, preferably both second system components have to satisfy the requirements so that there can be coupling to the first system component and operation of the suction pump. The data transmission is also preferably contactless in this case.

The apparatus according to the invention allows common use of system components only in the case of an admissible coupling thereof.

The invention claimed is:

1. An apparatus for recognizing couplings between a first component and a second component of a system, wherein one of the two components is provided with an identification unit and wherein a checking unit is operatively connected to the second component, wherein the identification unit contains an item of information relating to the first component, and wherein the checking unit is designed for recognizing and processing the item of information, wherein the checking unit moreover is designed such that, as a function of a result of the processing of the item of information, the checking unit is operatively connected to a barrier that allows or prevents an interconnection between the first and the second component.

2. The apparatus as claimed in claim 1, wherein the second component is a breastpump for expressing human breastmilk or a drainage pump for draining bodily fluids.

3. The apparatus as claimed in claim 1, wherein the first component is an accessory of the second component.

4. The apparatus as claimed in claim 3, wherein the first component is a breast shield of a breastpump for expressing human breastmilk or suction tubing or service tubing or a wound insert or a fluid collection container or a catheter.

5. The apparatus as claimed in claim 1, wherein the first component has a first coupling element and the second component has a second coupling element and wherein the two coupling elements are interconnected to establish the coupling.

6. The apparatus as claimed in claim 5, wherein the first and the second coupling elements are two complementary parts of a plug-in connection or a snap-on connection or a swivel connection or a bayonet connection or a magnetic connection or an electro-mechanical connection.

7. The apparatus as claimed in claim 5, wherein the identification unit and the checking unit are designed such that recognition and processing of the item of information is brought about when the coupling between the first and second coupling elements has not been brought about.

8. The apparatus as claimed in claim 1, wherein the checking unit has a radio-frequency identification (RFID) device.

9. The apparatus as claimed in claim 1, wherein the identification unit and the checking unit are designed such that transmission and/or recognition and/or processing of the item of information is brought about electronically or optically or chemically.

10. The apparatus as claimed in claim 1, wherein the identification unit and the checking unit are designed such that the item of information is transmitted contactlessly.

11. The apparatus as claimed in claim 1, wherein the checking unit is operatively connected to a switch that enables the operation of a suction pump in the case of an admissible coupling.

12. The apparatus as claimed in claim 1, wherein the barrier prevents a connection between the first and second coupling elements in the case of an inadmissible coupling.

13. The apparatus as claimed in claim 12, wherein the barrier is arranged on or in the second coupling element.

14. The apparatus as claimed in claim 1, wherein the system is a breastpump system for expressing human breastmilk or a drainage system for draining bodily fluids.

15. The apparatus as claimed in claim 1, wherein as a function of a result of the processing of the item of the information, the checking unit allows or prevents operation of the second component, wherein the second component case is a suction pump.

16. A method for recognizing couplings between a first and a second component of a system, wherein one of the two components contains an item of information relating to this first component, wherein a checking unit recognizes and processes the item of information and exerts an effect on the second component, wherein, as a function of a result of the processing of the item of information, the checking unit is operatively connected to a barrier that allows or prevents an interconnection between the first and the second component.

17. The method as claimed in claim 16, wherein the checking unit opens or closes a coupling element of the second component as a function of the result of the processing of the item of information.

18. The method as claimed in claim 16, wherein as a function of a result of the processing of the item of the information, the checking unit allows or prevents operation of the second component, wherein the second component is a suction pump.

* * * * *